United States Patent [19]

Cheng et al.

[11] Patent Number: 4,734,035

[45] Date of Patent: Mar. 29, 1988

[54] ENDODONTIC STOP POSITIONER

[76] Inventors: Fat-Hing Cheng; Chun-Hong Chan, both of 4th Floor, No. 301-63, Section 3, Hsitun Road, Taichung, Taiwan

[21] Appl. No.: 883,105

[22] Filed: Jul. 8, 1986

[30] Foreign Application Priority Data

Apr. 9, 1986 [TW] Taiwan .............................. 75203071

[51] Int. Cl.$^4$ .................................................. A16C 5/02
[52] U.S. Cl. ........................................ 433/102; 433/72
[58] Field of Search .......................... 433/102, 229, 72

[56] References Cited

FOREIGN PATENT DOCUMENTS 2404151 7/1975 Fed. Rep. of Germany ...... 433/102

Primary Examiner—Robert Peshock
Attorney, Agent, or Firm—Limbach, Limbach & Sutton

[57] ABSTRACT

An endodontic stop positioner combined with a reamer or a file used for taking a measurement of the root canal length of the tooth, includes a positioning body with a hard member and a soft member made of non-metal material, a central penetrating hole formed in the positioning body for accomodating the reamer or file, which reamer or file is movably held in the central penetrating hole for being inserted into the root canal of the tooth in taking the measurement in an X-ray, and at leat a wire disposed in a bottom center of the hard member and located in perpendicular intersection with the reamer or file. Consequently, the intersection point between the wire and the reamer or file can be clearly indicated in the X-ray for accurately measuring the root canal length of the tooth therewith.

1 Claim, 15 Drawing Figures (TOOTH STRUCTURE)

ENDODONTIC STOP POSITIONER

BACKGROUND OF THE INVENTION

This invention relates to an endodontic stop positioner with a positioning member and a wire intersectingly disposed in connection with a reamer or file movably held in the positioning member during endodontic therapy so as to clearly indicate the root canal length of the tooth in an X-ray film.

It is generally known that a human tooth as shown in FIG. 1, consists of pulp chamber 10, root canal 11, enamel 12, dentin 13, and cementum 14 wherein the pulp chamber 10 and the root canal 11 are composed of nerve tissue and blood vessels. Therefore, when the tissue of the pulp suffers from traumatic injury, caries and periodontal infection, inflammation or necrosis of the pulp tissue will occur. Consequently, an endodontic therapy generally called "root canal treatment" is necessary for this tooth. The main work required for the endodontic therapy is to thoroughly remove the inflammed or necrotic pulp tissue, and then to seal up the root canal with aseptic material. Since the kind of treatment is delicate work and has to be done within the inner part of a tooth, a radiographic diagnosis is usually relied upon to assist in completing the treatment. In order to successfully perform the endodontic therapy, the root canal length of the involved tooth must be exactly measured before the root canal is sealed up. Accordingly, the most important work in endodontic therapy is to measure the exact root canal length of the tooth because only when debridement is performed completely in the tooth can the root canal be sealed up thereat.

Concerning the measurement of the root canal length, various methods are adopted in endodontic therapy, and one of the frequently used methods is X-ray, for which a reamer or file 20, as shown in FIG. 2, is inserted into the root canal, and then an endodontic stop 30a movably attached to the reamer or file 20 is adjusted to have its bottom surface kept in contact with the incisal edge or the cusp tip of the tooth for being X-rayed thereat. In this condition, the intersection between the endodontic stop 30a and the reamer or file 20 in the root canal will be shown in the X-ray film so that the root canal length can be measured from the reamer or file 20.

A conventional endodontic stop is usually made of either metal or non-metal materials and is formed in a plate shape as shown in FIG. 3 wherein the endodontic stop 30b is a metal one. As the reamer or file 20 is made of metal material, the intersection point of the reamer or file 20 and the endodontic stop 30b appears as a blur in the X-ray, making it difficult to exactly estimate the root canal length. On the other hand, as a non-metal endodontic stop can be penetrated by the X-ray, no clear intersection point between the endodontic stop and the reamer or file can be seen in the X-ray film, particularly when the X-ray is taken at an inclined angle. As shown in FIG. 4, the endodontic stop 30a and the reamer or file 20 appearing in the X-ray intersect in an area rather than at a point, resulting in difficulty in determining the length of the root canal measured therewith.

SUMMARY OF THE INVENTION

It is accordingly a primary object of this invention to provide an endodontic stop positioner by which the root canal length of the tooth can be exactly measured for facilitating accurate and speedy endodontic therapy.

This and other objects are achieved by providing an endodontic stop positioner which comprises a positioning body combined of a hard member and a soft member made of non-metal material and having a penetrating hole formed in the center of the hard member for accommodating the reamer or file to be held and vertically moved therein, and at least a wire horizontally disposed in the bottom center of the hard member in perpendicular cross relation to the penetrating hole of the endodontic stop positioner. Consequently, the intersection point between the wire and the reamer of file can be clearly indicated in an X-ray for accurately measuring the root canal length therewith.

Further characteristics and advantages of this invention will become apparent from the following detailed description of examples of a preferred but not sole embodiment for the invention, given below with reference to the accompanying drawings,

DETAILED DESCRIPTION OF THE PREFERRED EMBODIMENT

Figure 1:
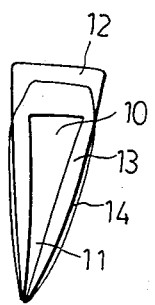
FIG. 1 is an illustrative view of the structure of a human tooth.
Figure 2:
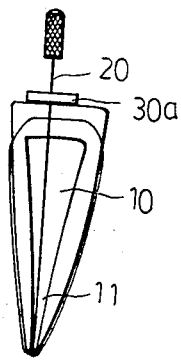
FIGS. 2 and 3 are illustrative views of the known endodontic stop matched with a reamer or file used for measuring the root canal length of an infected tooth.
Figure 3:
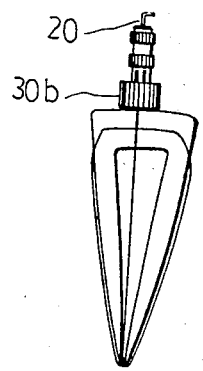
Figure 4A:
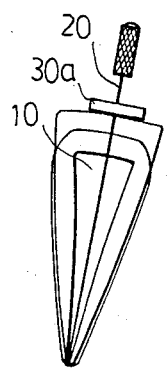
FIGS. 4 (A, B) is an illustrative view of the known endodontic stop coupled with a reamer or file and arranged in the infected tooth but X-rayed at an inclined angle.
Figure 4B:
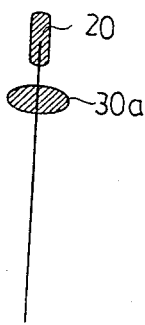
Figure 5:
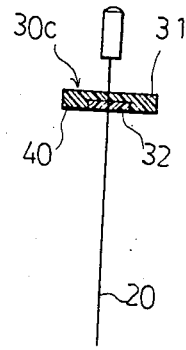
FIG. 5 is an illustrative view of a preferred embodiment of an endodontic stop positioner matched with a reamer or file according to this invention.
Figure 6B:
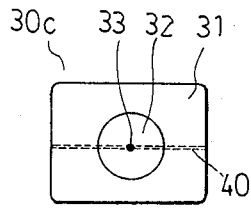
FIG. 6B is an enlarged top plane view of the preferred embodiment shown in FIG. 5.
Figure 6A:
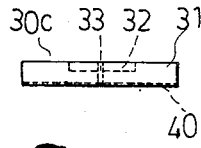
FIG. 6A is an enlarged side plane view of the preferred embodiment shown in FIG. 5.

Referring to FIGS. 5 and 6, there is shown a preferred embodiment of an endodontic stop positioner (E. S. P) according to this invention, which includes a positioning body 30c combined of a hard member 31 and a soft member 32. The hard member 31 is made of non-metal material (such as acrylic) with a recess formed in the middle thereof; the soft member 32 made of flexible non-metal material is attached in the recess with a penetrating hole 33 provided in the center of both members 31 and 32; and a wire 40, which is used as a reflecting medium, is horizontally embedded in the bottom center of the hard member 31 and located in perpendicular intersection with the reamer or file 20. As shown in FIG. 5, the reamer or file 20 is vertically held in the penetrating hole 33 of the positioning body 30c, which can be movably adjusted along the reamer or file 20. With the retaining force provided by the soft member 32 for the penetrating hole 33, the reamer or file 20 can be movably held in stable condition, and the positioning body 30c can also be adjusted up and down along the reamer or file 20.

Figure 7B:
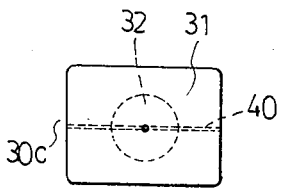
FIG. 7B is an enlarged top plane view of the preferred embodiment of FIG. 5.
Figure 8:
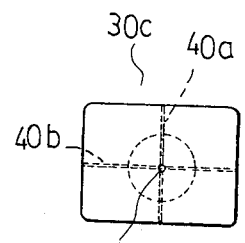
FIG. 8 is a top plane view of another alternative embodiment of the endodontic stop positioner shown in FIG. 5.
Figure 7A:
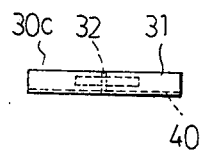
FIG. 7A is an enlarged side plane view of an alternative embodiment of the endodontic stop positioner of FIG. 5.

Referring to FIGS. 7 and 8, there is shown an alternative example of the endodontic stop positioner wherein the soft member 32 is completely embedded in the hard member 31 as shown in FIG. 7A, and a pair of wires 40a and 40b are arranged in a cross form in the bottom side of the hard member 31 as shown in FIG. 8 and intersecting at the penetrating hole 33.

Figure 9:
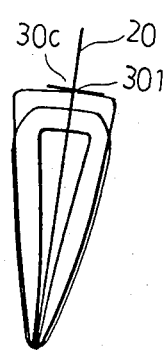
FIG. 9 is an illustrative view of the preferred embodiment of FIG. 5 as shown in an X-ray.
Figure 10:
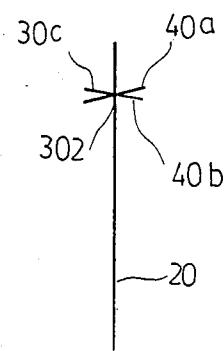
FIG. 10 is an illustrative view of the preferred embodiment of FIG. 8 matched with a reamer or file and shown in an X-ray.

Referring to FIGS. 9 and 10, the utilization of the preferred embodiment as described and illustrated hereinbefore can be clearly indicated when taken an X-ray. As shown in FIGS. 9 and 10, the intersecting points 301 and 302 of the embodiment of FIGS. 5 and 8 can be clearly seen in the X-ray.

Figure 11:
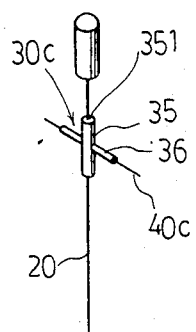
FIG. 11 is an illustrative view of another alternative embodiment of the endodontic stop positioner according to this invention.
Figure 12:
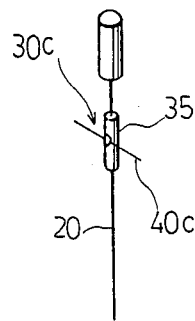
FIG. 12 is an illustrative view of still another alternative embodiment of FIG. 11.

Referring to FIG. 11, a further alternative example of the endodontic stop positioner according to this invention includes: a tubular body 35 made of non-metal material with a central through hole 351 longitudinally formed therein; a cross positioning member 36 located horizontally at the middle of the tubular body 35 with two portions extending therefrom in opposite directions; and a wire 40c fixed in a positioning member 36 across the central through hole 351. The file 20' is movably inserted into the central through hole 351 of the tubular body 35 in intersecting association with the wire 40c. It shall be appreciated that two or more cross positioning members 36 may be arranged in the tubular body 35. Alternatively, in the embodiment of FIG. 11, the wire 40c can directly arranged in the tubular body 35, as shown in FIG. 12, and located at a middle portion thereof in perpendicular intersection with the file 20 without the cross positioning member 36.

In a prolonged experiment conducted by the inventers, who are engaged themselves in dental service, every X-ray produced from the embodiments described and shown hereinbefore clearly indicated the intersecting point formed by the wire and the reamer or file, and no blur at the intersecting point, as can be seen from the known endodontic stop, has ever appeared.

While various advantageous embodiments have been chosen to illustrate the invention, it will be understood by those skilled in the art that many changes and modifications thereof can be made therein without departing from the scope of the invention as defined in the appending claims.

What we claim is:

1. An endodontic stop positioner comprising
   at least one metal wire; and
   a positioning body having a penetrating hole through which a reamer or file used to measure the root canal length of a tooth can pass, said positioning body being slidably along the reamer or file, said metal wire being installed in said positioning body and arranged to intersect with the penetrating hole of the positioning body; wherein said positioning body comprises
   a hard member and a soft member, said soft member being laid on or embedded in said hard member with the penetrating hole passing through both the hard member and the soft member so that the reamer of file located in the penetrating hole is subject to a retaining force effected by the soft member for facilitating the positioning of the positioning body along the reamer;
   thereby, in an X-ray, the intersection point between said metal wire and the reamer or file can be clearly indicated for accurately measuring the root canal length of the tooth.

* * * * *